(12) United States Patent
Miller et al.

(10) Patent No.: US 10,447,661 B1
(45) Date of Patent: *Oct. 15, 2019

(54) SYSTEM AND METHOD FOR PRIVACY-PRESERVING GENOMIC DATA ANALYSIS

(71) Applicant: Quintiles IMS Incorporated, Danbury, CT (US)

(72) Inventors: Ronald A. Miller, Falls Church, VA (US); Luther Dunlap, West Grove, PA (US); Kenneth Park, New Market, MD (US); John Muller, Malvern, PA (US); Dave Shell, Collegeville, PA (US)

(73) Assignee: IQVIA Inc., Parsippany, NJ (US)

(*) Notice: Subject to any disclaimer, the term of this patent is extended or adjusted under 35 U.S.C. 154(b) by 465 days.

This patent is subject to a terminal disclaimer.

(21) Appl. No.: 15/390,379

(22) Filed: Dec. 23, 2016

(51) Int. Cl.
H04L 29/06 (2006.01)
H04L 9/32 (2006.01)
G16B 50/00 (2019.01)

(52) U.S. Cl.
CPC .......... *H04L 63/0428* (2013.01); *G16B 50/00* (2019.02); *H04L 9/3236* (2013.01)

(58) Field of Classification Search
CPC .... H04L 63/0428; H04L 9/3236; G16B 50/60
USPC ........................................................ 713/168
See application file for complete search history.

(56) References Cited

U.S. PATENT DOCUMENTS

| | | |
|---|---|---|
| 10,013,575 B2 | 7/2018 | Hubaux et al. |
| 2013/0044876 A1 | 2/2013 | Shaw et al. |
| 2013/0266135 A1 | 10/2013 | Pratt |
| 2014/0289536 A1* | 9/2014 | MacCarthy .............. H04L 9/008 713/189 |
| 2016/0125141 A1* | 5/2016 | Raisaro .................. H04L 9/008 713/189 |
| 2017/0005787 A1* | 1/2017 | Weaver .................. G16H 50/30 |

OTHER PUBLICATIONS

Popic and Batzoglou, "Privacy-Preserving Read Mapping Using Locality Sensitive Hashing and Secure Kmer Voting," bioRxiv [doi: http://dx.doi.org/10.1101/046920], Apr. 3, 2016, 14 pages.

* cited by examiner

*Primary Examiner* — Samson B Lemma
*Assistant Examiner* — Carlos E Amorin
(74) *Attorney, Agent, or Firm* — Fish & Richardson P.C.

(57) ABSTRACT

A method includes accessing genomic data of from a genomic database; generating, by a processor, a first hash by probabilistically and irreversibly encrypting a first portion of the genomic data encoding the first genomic sequence, the first hash projecting the first portion into reduced dimensions such that the first portion of the genomic data encoding the first genomic sequence becomes statistically improbable to recover outside the first processor; generating, by the processor, a first cryptogram by deterministically and reversibly encrypting a second portion of the genomic data encoding the first genomic sequence; generating, by the processor, a look-up table by using at least the first cryptogram as a key and the first portion of the genomic data encoding the first genomic sequence as the value, and transmitting data encoding the first hash and the first cryptogram to one or more processors that are different from the first processor.

26 Claims, 6 Drawing Sheets

| # Chromosome | Position | ... | REF Gene | Alteration | ... |
|---|---|---|---|---|---|
| ... | | | | | ... |
| ... | | | | | ... |

FIG. 3

| Token | Encrypted PII | Locus | Encrypted Genomic Data |
|---|---|---|---|
| ⋮ | ⋮ | ⋮ | ⋮ |
| ⋮ | ⋮ | ⋮ | ⋮ |

410 → table; 411 Token, 412 Encrypted PII, 413 Locus, 414 Encrypted Genomic Data

FIG. 4B

SYSTEM AND METHOD FOR PRIVACY-PRESERVING GENOMIC DATA ANALYSIS

BACKGROUND

Genomic data may be more and more available, giving rise to a myriad of analysis.

SUMMARY

In one aspect, some implementations provide a computer-implemented method that includes accessing, by a first processor, genomic data of a particular patient from a genomic database, the genomic data encoding strings of nucleotide values from genomic sequences of the particular patient as well as information of respective chromosomes on which corresponding genomic sequences reside; generating, by the first processor, a first hash by probabilistically and irreversibly encrypting a first portion of the genomic data encoding a first genomic sequence, the first hash projecting the first portion into reduced dimensions such that the first portion of the genomic data encoding the first genomic sequence becomes statistically improbable to recover outside the first processor; generating, by the first processor, a first cryptogram by deterministically and reversibly encrypting a second portion of the genomic data encoding the first genomic sequence, the first portion and the second portion being non-overlapping; generating, by the first processor, a look-up table by using at least the first cryptogram as a key and the first portion of the genomic data encoding the first genomic sequence as the value, and transmitting, by the first processor, information encoding the first hash and the first cryptogram to one or more processors that are different from the first processor and without patient identifiable information.

Implementations may include one or more of the following features.

The first portion may include locus information that includes an identification (ID) of a particular chromosome on which the first genomic sequence resides as well a starting position of the first genomic sequence on the particular chromosome. The second portion may include strings of nucleotide values from the first genomic sequence. The method may include generating, by the first processor, a second hash by deterministically encrypting the first portion of the genomic data.

Generating the look-up table may include: using the second hash as well as the first cryptogram as a key and the first portion of the genomic data encoding the first genomic sequence as a value such that the first portion of the genomic data encoding the first genomic sequence is retrievable at the first processor based on the combination of the second hash and the first cryptogram. Transmitting the information may include transmitting the information encoding the first hash, the second hash, and the first cryptogram to one or more processors that are different from the first processor and without patient identifiable information.

The method may include: generating, by the first processor, a third hash by performing a probabilistic and irreversible hashing on the first portion of the genomic data encoding a second genomic sequence, the third hash projecting the first portion into reduced dimensions such that the first portion of the genomic data encoding a second genomic sequence becomes statistically improbable to recover outside the first processor.

The method may include: generating, by the first processor, a second cryptogram by deterministically and reversibly encrypting a second portion of the genomic data encoding the second genomic sequence. The method may include: adding, by the first processor, a new key-value entry to the look-up table using at least the third hash as a key in the new key-value pair and the second cryptogram as a value for the new key-value pair. The first hash and the third hash may both point to chromosomal information from the same patient. The first hash and the second hash may point to chromosomal information from different patients.

Probabilistically and irreversibly encrypting may include performing a locality-sensitive hashing. Deterministically encrypting the string of nucleotide values may include using a reversible hash to encrypt the string of nucleotide values. Deterministically encrypting the string of nucleotide values may include encrypting using a key.

The information encoding the string of nucleotides values of the particular chromosome may include a reference genome sequence and an alteration sequence.

In another aspect, some implementations provide a computer system that includes at least one processor configured to perform the operations of: accessing genomic data of a particular patient from a genomic database, the genomic data encoding strings of nucleotide values from genomic sequences of the particular patient as well as information of respective chromosomes on which corresponding genomic sequences reside; generating a first hash by probabilistically and irreversibly encrypting a first portion of the genomic data encoding the first genomic sequence, the first hash projecting the first portion into reduced dimensions such that the first portion of the genomic data encoding the first genomic sequence becomes statistically improbable to recover outside the computer system; generating a first cryptogram by deterministically and reversibly encrypting a second portion of the genomic data encoding the first genomic sequence, the first portion and the second portion being non-overlapping; generating a look-up table by using at least the first cryptogram as a key and the first portion of the genomic data encoding the first genomic sequence as the value, and transmitting information encoding the first hash and the first cryptogram to one or more processors that are different from the computer system and without patient identifiable information pointing to the particular patient.

Implementations may include one or more of the following features.

The computer system may perform the operations of: generating a second hash by deterministically encrypting the locus information of the first chromosome. Generating the look-up table may include: using the second hash as well as the first cryptogram as a key and the first portion of the genomic data encoding the first genomic sequence as a value such that the first portion of the genomic data encoding the first genomic sequence is retrievable at the first processor based on the combination of the second hash and the first cryptogram. Transmitting the information may include transmitting the information encoding the first hash, the second hash, and the first cryptogram to one or more processors that are different from the first processor and without patient identifiable information.

The computer system may perform the operations of: generating a third hash by probabilistically and irreversibly encrypting the first portion of a second genomic sequence, the third hash projecting the first portion into reduced dimensions such that the first portion of the genomic data encoding the second genomic sequence becomes statistically improbable to recover outside the first processor;

The computer system may perform the operations of: generating a second cryptogram by deterministically and reversibly encrypting a second portion of the genomic data encoding the second genomic sequence.

The computer system may perform the operations of: adding a new key-value entry to the look-up table using at least the third hash as a key in the new key-value pair and the second cryptogram as a value for the new key-value pair. Probabilistically and irreversibly encrypting may include performing a locality-sensitive hashing. Deterministically encrypting the string of nucleotide values may include using a reversible hash to encrypt the string of nucleotide values. Deterministically encrypting the string of nucleotide values may include encrypting using a key.

In yet another aspect, some implementations may provide a computer-readable medium comprising software instructions that, when executed by a computer, causes the computer to perform the operations of: accessing genomic data of a particular patient from a genomic database, the genomic data encoding strings of nucleotide values from genomic sequences of the particular patient as well as information of respective chromosomes on which corresponding genomic sequences reside; generating a first hash by probabilistically and irreversibly encrypting a first portion of the genomic data encoding the first genomic sequence, the first hash projecting the first portion into reduced dimensions such that the first portion of the genomic data encoding the first genomic sequence becomes statistically improbable to recover outside the computer; generating a first cryptogram by deterministically and reversibly encrypting a second portion of the genomic data encoding the first genomic sequence, the first portion and the second portion being non-overlapping; generating a look-up table by using at least the first cryptogram as a key and the first portion of the genomic data encoding the first genomic sequence as the value, and transmitting information encoding the first hash and the first cryptogram to one or more processors that are different from the computer and without patient identifiable information The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

FIG. 3 shows an example of genomic data arrangement for efficient retrieval.

FIG. 4B shows an example of a hash table as generated and used in the vault for patient identifiable information.

Like reference symbols in the various drawings indicate like elements.

DETAILED DESCRIPTION

Figure 1:
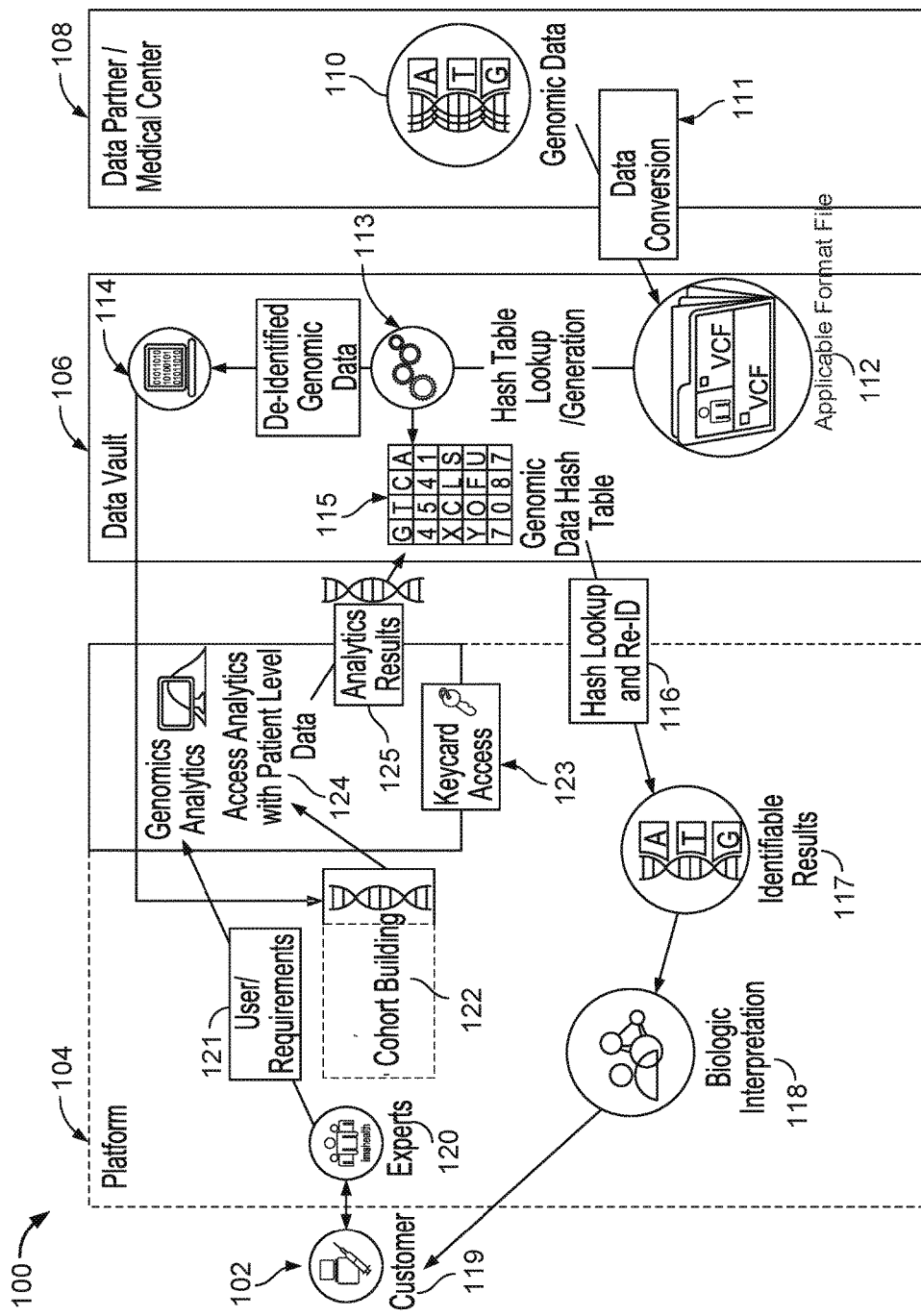
FIG. 1 illustrates an example of a model in which genomic data from various patients are aggregated and de-identified for genomic analytics while the analytics results are capable of being re-identified.

This disclosure generally describes a system and method to preserve privacy for large scale genomic data analysis. Performing an epidemiological investigation into the correlation of genetic expressions and medical expressions is computationally intensive. The sheer size of the human genome (~3 billion base pairs residing on 23 chromosomes) leads to exponential number of permutations that impose a tremendous computational burden in managing a database of genomic data. Relating this genetic information between individuals is further complicated (i) where genetic information sometimes differs slightly in relative location, (ii) when phenotype traits are considered in association with other genetic expression residing elsewhere on the same chromosome, and (iii) when other disease states mimicking a disease state is being investigated. These computational burdens may be exacerbated when a database of genomic data is further de-identified and correlated with other information descriptive of other diagnostic tests, assessments, and treatment data. One or more data sources (for example, one or more genomic data acquisition centers) may introduce flawed data at rate significant enough to complicate correlation analysis. Every quantum of error may spawn countless combinatorial analysis in order to establish the requisite degree of correlation. Thus, configuring a computer system to encode genomic data with accuracy can facilitate rapid correlation of genetic and medical data by saving countless CPU cycles in correlation analysis and arriving at results with increased efficiency in epidemiological investigations.

Public concern over patient privacy gives rise to the desire for anonymity. A number of techniques can be employed for de-identifying patients' genomic variances. De-identifying patient identifiable genomic variances ("PII" or patient identifiable information) from a reference human genome may be a pre-requisite to epidemiological studies where patient privacy is paramount. HIPPA and analogous international laws may not permit health care providers to obtain large genomic samples to perform epidemiological studies unless mechanisms are in place to ensure patient privacy.

To illustrate the privacy concern, consider an example of an epidemiological study that involves the following organization entities: (1) the trusted $1^{st}$ party permitted to retain PII, (2) an untrusted $2^{nd}$ party as the recipient of de-identified data and can perform epidemiological investigation based on the de-identified data, and (3) and trusted $3^{rd}$ party that can both de-identify and re-identify genomic data.

In the context of a multi-party investigation, de-identification techniques may be broadly classified into 3 categories: (i) deterministic and non-reversible scrambling via either hashing or public/private key encryption; (ii) deterministic and reversible scrambling via either hashing or public/private key encryption; and (iii) probabilistic and non-reversible scrambling that, while making patient identification statistically improbable for the third parties performing correlational analysis, retains enough variant information to allow for cross-patient analysis. Here, scrambling refers to general encryption techniques. Such techniques include positional manipulations such as permutation, rearrangement, and resorting. These techniques also include logic operations such as mixing and xor (exclusive or). These techniques further include functional operations that project an input having a first dimensionality (aka cardinality) to an output having a second dimensionality (cardinality). Within the confines of this document, scrambling, encrypting, and encoding may be used interchangeably to encompass any of the above identified operations.

With regard to the first and second deterministic methods described above, neither of these deterministic methods may allow for epidemiological investigation by untrusted third parties. This is because the encrypted genomic data would have another variant at a close-by chromosomal location position placed into, for example, a Hash Value very far from the Hash Value for the original position. In short, deterministic hashes result in random information that can't be correlated across patients. Also bear in mind that epidemiological studies generally involve the correlation of multiple base pair variants and their relative loci. While some implementations may use Locality Sensitive Hashing ("LSH") to achieve probabilistic scrambling of the genomic sequence to facilitate subsequent search and compare operations, these implementations may prevent re-identification of patients and any one of their variant/loci of interest as the result of an epidemiological investigation. Yet, re-identification by either the trusted $3^{rd}$ party or the $1^{st}$ party may be advantageous for identifying pathological genetic markers as well as eventual and desired treatments for patients.

Some implementations discussed herein combine deterministic and reversible scrambling with probabilistic yet irreversible scrambling. For example, the de-identification may involve (i) probabilistic and irreversible hashing of a first portion of the genomic data that encodes, for example, information of the chromosome on which the genomic sequence resides as well as information of the location on the chromosome where the genomic sequence resides; and (ii) deterministic and reversible encryption of a second portion of the genomic data such as the genomic sequencing data. In some instances, the first portion may refer to the locational information of which chromosome and starting position the genomic sequence occupies. The second portion, on the other hand, may refer to a reference genomic sequence ("REF") and an alteration from the genomic sequence ("ALT"), when REF and ALT are not SNPs. The information of the chromosome on which the genomic sequence resides as well as information of the location on the chromosome where the genomic sequence resides may be jointly referred to as the locational information or Locus information. The probabilistic hashing allows the second portion of the genomic data to be projected into a sufficiently smaller number of buckets such that recovery of the second portion of the genomic data becomes statistically improbable. The reduction in dimensionality is significant enough to foreclose the statistical likelihood of reversely constructing a one-to-one correspondence between the hashed second portion and the unhashed second portion such that deriving the unhashed second portion of the genomic data based on the hashed information is statistically improbable. With the second portion of the genomic data (including locational information) concealed, the privacy of the genomic data can be further preserved while the efficiency of genomic pattern matching/recognition may be enhanced. In the unlikely event when the encryption key is breached or when hackers have decrypted the genomic sequence data (e.g., through brute force searching), the hashed second portion of genomic data remains irreversible. Without the locational information from the second portion, the genomic sequence data itself is still inadequate to be linked to any individual patient. In these implementations, patient privacy can be enforced to alleviate concerns of having genomic data processed by third parties in a distributed manner while enabling statistical analysis by virtue of retaining the ability to perform re-identification of individual genomic variants of interest when the processed genomic data arrive at a trusted party. Within a trusted data vault that performs the deterministic encryption that is reversible and the probabilistic hashing that is irreversible, a look-up table may be constructed by using the encrypted genomic sequence data as the key and the actual location information as the value. Upon receiving the processed genomic data, the trust data vault may recover the actual location information, and decode the encrypted genomic sequence data, to the extent necessary. Here, when encrypted data includes an encrypted hash, a deterministic hash can be used for decoding.

Within the confines of this specification, the following terms are used.

"Hash Function" Any function that can map input data of an arbitrary size to output data of a fixed size.

"Hash Values" The result of applying a hash function to input data. The output of a Hash Function.

"Key Space" The integer number count of all possible Hash Values for a given Hash Function.

"Deterministic Hash" A Hash Function which results in a deterministic one-to-one mapping of input data to a Hash Values.

"Probabilistic Hash" A Hash Function which results in a non-deterministic mapping of input data to a Hash Value or Hash Values. Here, non-deterministic means either that the same input value does not always result in the same Hash Value, or that many input values map to the same Hash Value.

"LSH" Locality Sensitive Hashing. A Probabilistic Hash that reduces the cardinality of high-dimension input data into a smaller Key Space in which similar inputs are more likely to be in the same output bucket.

"Locus" (plural "Loci") Any value that is a representation of chromosome and position within a chromosome of a base-pair, genetic variant to a reference genome, or polymorphism. This can be the chromosome number and position combined, an encrypted value thereof, a Hash Value thereof, and with or without transformation of chromosome number and position.

"Obfuscated Locus" (plural "Loci") A locus that has been obfuscated, encrypted, hashed, or otherwise scrambled.

"PII" Patient Identifiable Information. Any information that directly or indirectly identifies an individual from any information pertaining to their healthcare.

"De-ID" De-Identification. The act of obfuscating, hiding, removing, encrypting, hashing or otherwise scrambling PII such that the result no longer can be used to identify an individual.

"First Party" ("$1^{st}$ Party") a legal entity that is the steward of PII genomic data.

"Trusted Third Party" ("TTP") a legal entity entrusted with PII genomic data as well as the de-identification of it.

"Untrusted Second Party" (Untrusted $2^{nd}$ Party) a legal entity that cannot be entrusted with PII.

"Re-identification" The act of reversing a hash, encryption cipher, or other scrambling or obfuscating method for a single genomic variant. The result of Re-identification is not PII because it only identifies a single variant within a patient's genome.

"SNP" Single nucleotide polymorphism is the most common type of genetic variation among people. Each SNP represents a difference in a single DNA building block, called a nucleotide.

FIG. 1 illustrates an example of a model 100 in which genomic data from various patients are aggregated and de-identified for genomic analytics while the analytics results are capable of being re-identified. Data partner 108 may include a medical center, a research institute, a clinic, a lab, or any facility in which genomic data 110 may be acquired from a human subject. In some instances, data partner 108 may operate on a DNA sample of a human subject. The operation may include sequencing DNA by, for example, bridge PCR (polymerase chain reaction) in which fragments are amplified upon primers attached to a solid surface and form "DNA colonies" or "DNA clusters". The sequencing operation may also include high-throughput methods that parallelize the sequencing process, produce thousands or millions of sequences concurrently. The operations may also include the assembly of the DNA sequence to create a representation of the original chromosome, and the annotation and analysis of that representation. These operations produce genomic data 110. In these data centers, genomic data 110 may include encrypted patient identifiable information (PII). The encryption may be performed with a variety of symmetric keys as well as resorting to public/private key pairs from PKI infrastructure. As genomic data 110 from various data centers may vary in format, a conversion process 111 may be in place to generate a consistent layout of genomic data 111 from different data centers as such data enter data vault 106. The consistency connotes uniformity and facilitates more efficient data processing.

As illustrated in FIG. 1, the genomic data entering data vault 116 is converted into an applicable format file 112. In one example, the applicable format file 112 includes fields encoding the chromosome identification (ID) number of the chromosome where a particular genomic sequence resides, the position on the strand of chromosome where the residing genomic sequence starts, the reference genomic sequence, and the alteration representing deviations from the reference. The alterations from reference genomic sequences are also known as variations or variants. The alterations may contain significant differences between subjects. To improve performance of de-identification and re-identification, some implementations may opt to apply encryption to the variations but not the reference. As illustrated, the application format file 112 may also contain header information or metadata. Examples include indications of a tissue source, a sample date, a sequencing date, a sequencing platform, a methodology of sequencing, a sequencing facility, an ordering physician, and a date of order. The header information or metadata may also contain personally identifiable information in the form of a patient name, a Medical Record Number, an address, etc. Such information may be de-identified using double encryption techniques.

The applicable format file 112 may be processed (113) to generate the genomic data hash table 115 and the de-identified chromosomic data 114. In one example, the payload data from the applicable format file 112 may be processed to de-identify genomic data. The payload data may include, for example, the chromosome ID of the chromosome on which the genomic sequence resides, the position on the chromosome where the genomic sequence starts (measured in base pairs), the reference genomic sequence, and the alteration/variation from the reference. In one illustration, the applicable format file may be based on the nucleotide value(s) (A, T, C, or G), chromosome, and chromosomal location(s) including insertions or deletions. In this illustration, this chromosomal location data is used to generate a unique location dependent hash for each variant that will be securely stored separately from the nucleotide values of the genomic information. In some implementations, a deterministic and reversible encryption method is applied to the nucleotide values of the genomic information including the reference sequence as well as the alteration sequence whenever multiple base pairs constitute a particular variant being de-identified. In some implementations, the deterministic and reversible encryption is applied to only the alteration sequence when the reference genomic sequence is static and known. The deterministic and reversible encryption may also be applied to the information field in the header of the applicable format file. Concurrent to this deterministic and reversible hashing in the form of, for example a locality sensitive hash ("LSH") is applied to the chromosomal locational information for each chromosome of the genomic sequences, including the chromosomal ID of the particular chromosome and the position on the chromosome where the genomic sequence starts. The starting position of the genomic sequence on the chromosome may be measured in terms of number of offset base pairs. This locality sensitive hash may map the chromosomal location information into a sufficiently small number of buckets to provide statistical improbability of identifying a patient. Particularly, the locality sensitive hash will reduce the chromosomal information into smaller dimensions (also known as cardinalities) with high collision likelihood such that the hashed value has high probability of collision when the input values are highly similar. Effectively, many variants with statistically similar loci are mapped into the same bucket. Such hashed values are not reversible. Indeed, this m to 1 mapping (where m is larger than one) renders it statistically improbable to recover the location information once hashed. The hashed value may be transmitted to third-party data processing centers. The LSH provides a "fuzzy" locality for the encoding process since it's not exact but still packs the genomic variants into buckets of Hash Values that are lexicographically near to one another with respect to their loci. Indeed, the number of buckets is changeable; and it is what reduces the cardinality of the probability space. This reduction may form one central parameter that can be tuned to balance the need for reduction of cardinality and perseverance of locality. For a fined tuned LSH, re-identifying patient information (such as positional information) from the combination of the hashed chromosomal information and the encrypted genomic information is statistically improbable. In this manner, all genetic variants can be consistently encoded to create an array of markers that retain information of genetic variation and relative genomic position, without actually revealing identifiable sequence data.

The goal of the LSH method is to hash input information into buckets, expecting that the most similar or near-duplicate input information will hash into the same bucket(s). This is the opposite of a classical Deterministic Hash function where the aim is to avoid collisions between similar inputs.

In LSH, the input information (also known as an input object) is projected into a low-dimensional space where each input data point is mapped to a vector called a signature. The signatures can then be assigned to one of a plurality of buckets. Similar input objects are thereby mapped to the same buckets with a high probability. This is achieved using a hashing family K, or set of k hash functions, where each hash function must satisfy the locality sensitive hashing property defined on a space R with a given distance measure d:

A family K of hash functions is said to be $(d_1, d_2, p_1, p_2)$-sensitive if for any x and y in R:

a. If the distance between objects x and y, $d(x,y) \leq d_1$, then for all hash functions k in K: the probability that the hash of x is equal to the hash of y is at least equal to $p_i$, the recall rate, i.e., $p[k(x)=k(y)] \geq p_1$; and b. If the distance $d(x,y) \geq d_2$, then for all k in K: $p[k(x)=k(y)] \leq p_2$, the collision error rate.

Similarly, statements a) and b) can be expressed in terms of similarity, i.e., if the similarity $sim(x,y) \geq s_1$, $p[k(x)=k(y)] \geq p_1$ and if the similarity $sim(x,y) \leq s_2$, then for all k in K: $p[k(x)=k(y)] \leq p_2$. In both forms, the recall rate $p_1$ is expected to be greater than the collision error rate $p_2$.

In selecting the family of hash functions to be used (e.g., based on a training set of objects), the $(d_1, d_2, p_1, p_2)$-sensitive criteria a) considers only those objects with a high probability of collision (low distance/high similarity between them) and requires selection of a family of hash functions which provide a high probability that these will be assigned to the same bucket, while the $(d_1, d_2, p_1, p_2)$-sensitive criteria b) considers only those objects with a low probability of collision (high distance/low similarity between them) and requires a family of hash functions which provide a low probability that these will be assigned to the same bucket. Both criteria are met in the family of hash functions which are selected for use in the method.

The distance (or similarity) can be, for example, the cosine distance, Hamming distance, Jaccard similarity, or the like. The Jaccard similarity (or Jaccard Index), for example, measures similarity of two sets as the ratio of the size of their intersection to the size of their union. LSH family implementations are available for Hamming distance (bit sampling), Jaccard Similarity (MinHash, or SimHash) and Cosine (Random hyperplane hashing). For example, MinHash is an LSH family for the Jaccard index. The MinHash is used to compute an estimate of the Jaccard similarity coefficient of pairs of sets, where each set is represented by an equal-sized signature derived from the minimum values of the hash function. Random projection is an LSH family for the Cosine similarity.

Thus, given the selected family of hash functions, the projection for each input object is hashed with each function in the family to generate a hash, and the set of hashes for the input object are combined, e.g., concatenated, to form a multidimensional output object of length k, which may form a central parameter for fine-tuning to balance the need for reduction of cardinality and perseverance of locality indication (e.g., similar locales with high Jaccard similarities are more likely to be mapped to the same output bucket). Indeed, the reduction renders the recovery of the locality information statistically unlikely and thus effectively prevents the genomic sequence data (even encrypted) from being linked to a chromosomal location. In some implementations, this output object is the Obfuscated Locus. In these implementations, the Obfuscated Locus and the encrypted genomic sequence information form the de-identified genomic data 114 and are subsequently sent to data processing centers.

This de-identified genomic data 114 can be statistically analyzed to support research on genetic associations or to guide clinical care at platform 104 by third parties. Within data vault 106, hash table 115 may be constructed as a look-up table to have each encrypted genetic variant data as the key with the corresponding actual locality information as the value. Based on this hash table 106, once analysis (125) of the encrypted genomic data 114 has been completed and results have been returned to data vault 106, the encrypted genomic data 114 may be linked to the actual locality information so that the analysis results are linked to the corresponding actual location. In some implementations, this recovery process involves a table lookup using the encrypted genomic data 114 as the key to retrieve the chromosomal location information corresponding to the genomic data. As discussed herein, the chromosomal location information includes the chromosome ID as well as the starting position of the genomic sequence on the chromosome. The starting position on the particular chromosome may be an offset position and measured in base pairs. The genomic sequence, without being linked to the chromosomal location, may not be specific to each individual. In these implementations, only the encrypted genomic sequence data may be used as the key in hash table 115. Each encrypted genomic data may be mapped to a corresponding chromosomal location. The encrypted genomic data may thus be used to recover the actual chromosomal location once the analysis results come back from data processing centers.

In platform 104, genomic analytics (124) may be performed on the encrypted genomic data 114 along with hashed chromosomal location information. The analysis may include correlation of genetic data and chromosomal information from various patients. For example, various groups of patients may be classified based on their genetic variations as well as phenotypical differences. Here, a phenotype refers to the observable physical or biochemical characteristics of an organism, as determined by both genetic makeup and environmental influences. This patient-to-patient classification may be part of a process to build a cohort of patients with particular expressions or inclinations (122). Here, a cohort refers to a group of subjects/patients who share a defining characteristic (typically subjects/patients who experienced a common event in a selected time period, such as diabetes, allergy, and cardiac arrest). The analysis may also include correlating various genetic data and chromosomal information from the same de-identified patient with a target genetic information. For example, the target genetic information may correspond to a gene known for promoting or inhibiting particular conditions. In some cases, the target genetic information may be the result of previous cohort-building process that reveals the target genetic information as highly correlated to certain phenotypic conditions, such as, for example, allergy, cardiac arrhythmia, diabetes, and dementia. The genomic analytics may be performed with keycard access (123) such that only a combination of operators having a physical key/token may inspect the encrypted genomic data along with the hashed chromosomal locality information. The genomics analytics process may receive user input from an expert 120 so that correlation analytics may be fine-tuned and targeted at particular genetic variations.

A single variant of interest in the encrypted genomic data, once re-mapped to the actual chromosomal location, may be re-identified (116) for a particular, still anonymous patient (or a cohort of patients). The re-identified results 117 may be correlated with biologic information 118 that includes, for example, physiologic conditions, hereditary traits, protein structure, additional genomic association study data, and disease status. The linkage may then be provided to customer 102. Customer 102 may interact with expert 120 who may adjust user input to fine tune the genomics analytics process. The user input may adjust the target genetic information to search for. The user input may also narrow down to broaden up the cohort groups for statistical determination of customer 102 being a member.

Figure 2:
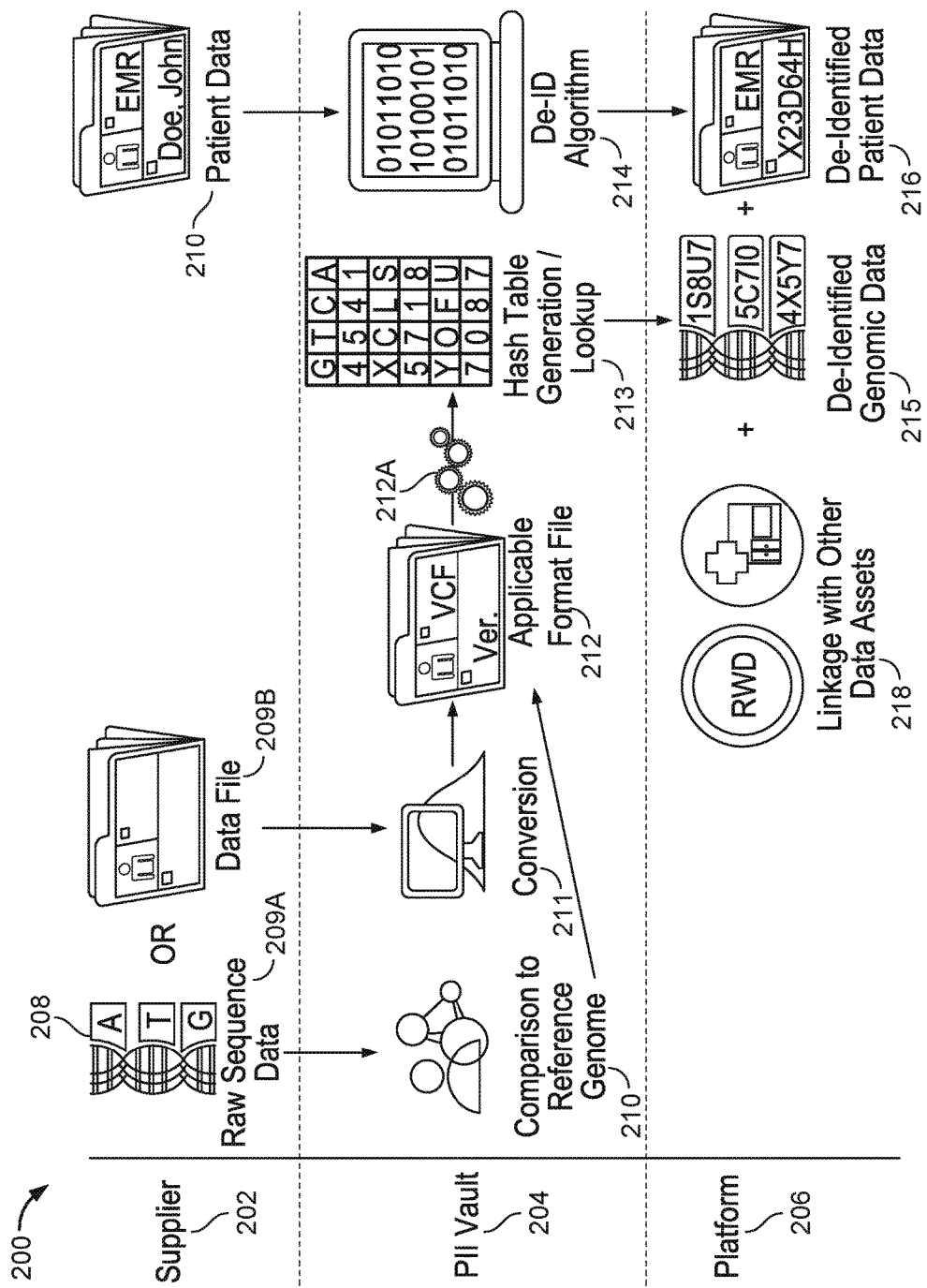
FIG. 2 is a layered diagram showing data exchange between data suppliers, a vault for patient identifiable information, and a platform of integration.

FIG. 2 is a layered diagram showing data exchange between data supplier 202, a vault 204 for patient identifiable information, and a platform 206 for integration of data. In this diagram, data supplier 202 may include genomic data provider 108 of FIG. 1 that generates raw sequence data 209A or a proprietary format data 209B. Data suppler 202 may also generate patient data 210 that has been obtained from, for example, pharmacies. Such patient data 210 may include, for example, prescription information indicating prescription filled for the patient. In this example, this patient data 210 follows a specific format for efficient and robust de-identification that includes double encryptions.

At data vault 204, raw sequence data 209 may be compared to reference genome 210 and then converted into applicable format file 212. As discussed in association with FIG. 1, the applicable format file 212 may include fields encoding the chromosome identification (ID) number of the chromosome where a particular genomic sequence resides, the position on the strand of chromosome where the residing genomic sequence starts, the reference genomic sequence, and the alteration representing deviations from the reference. The alterations from reference genomic sequences are also known as variations or variants. As illustrated, the application format file 112 may also contain header information or metadata. Examples include indications of a tissue source, a sample date, a sequencing date, a sequencing platform, a methodology of sequencing, a sequencing facility, an ordering physician, and a date of order. The header information or metadata may also contain personally identifiable information that can be de-identified using double encryption techniques. Similarly, proprietary file 209B may be converted into applicable format file 212.

The applicable format file 212 arranges information in advantageous layout such that access to the genomic information may be expeditiously processed using state of the art storage and retrieval technologies.

Figure 3:
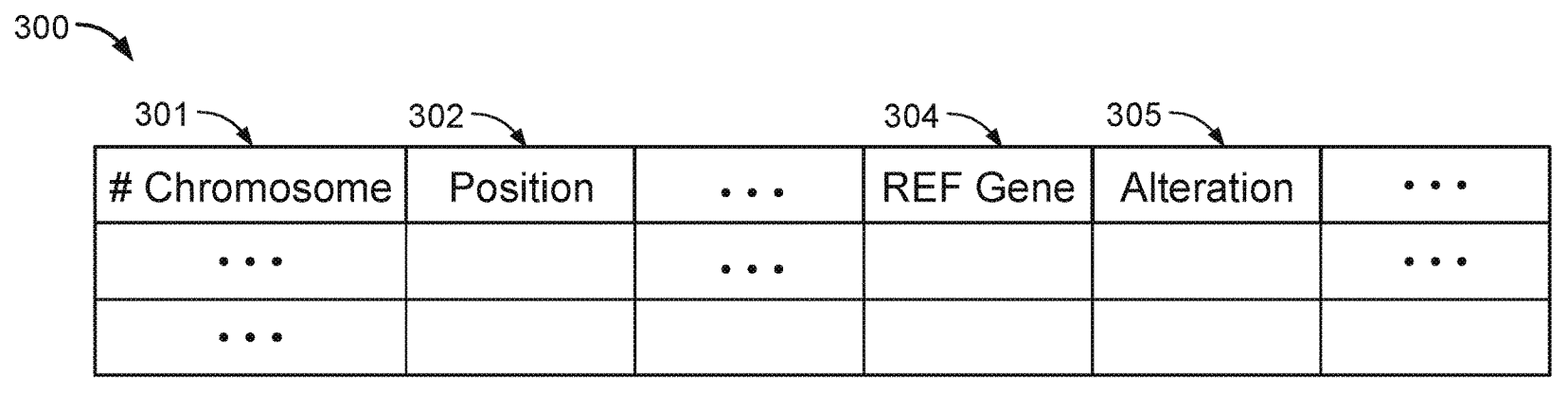
Figure 4A:
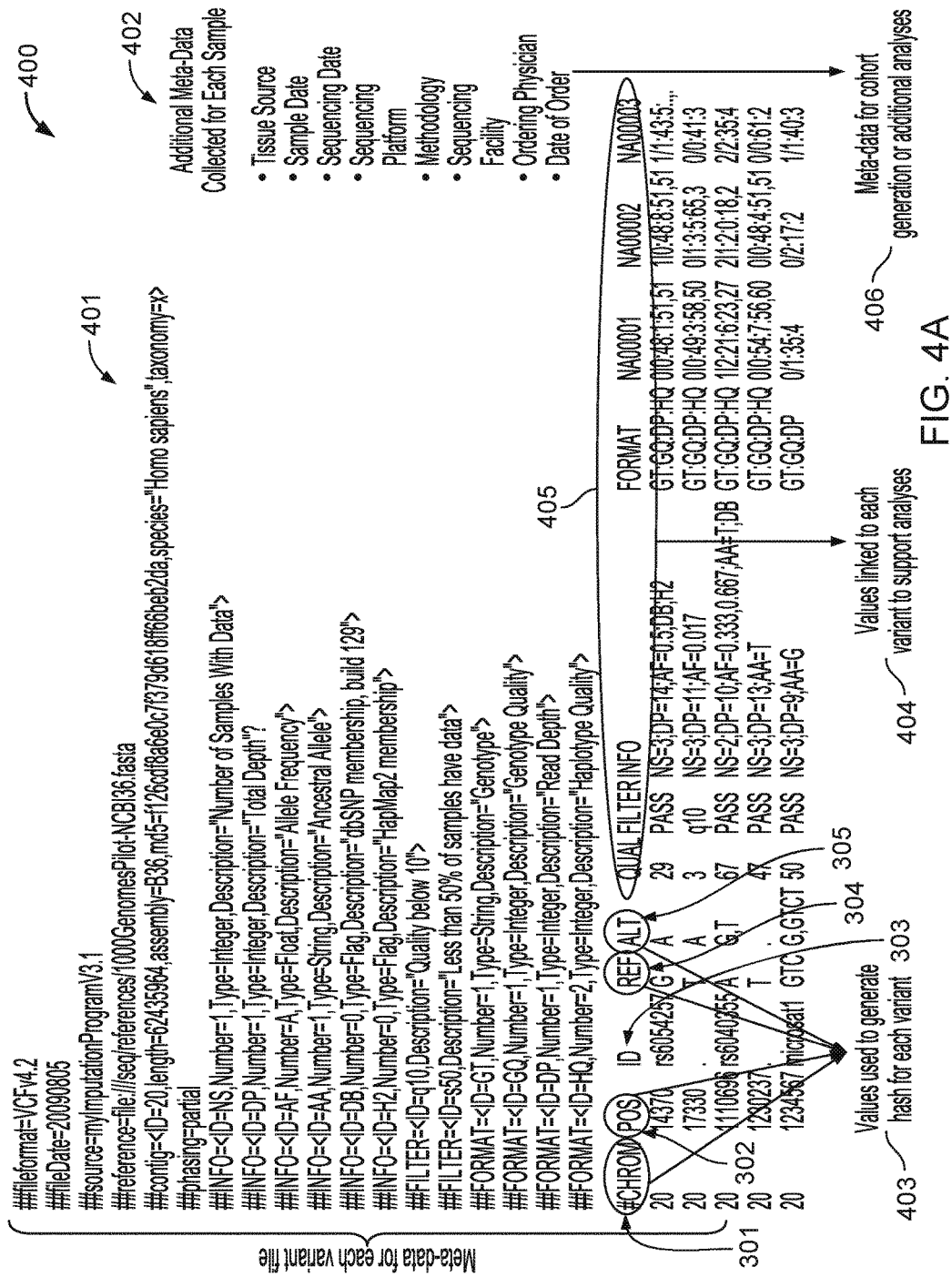
FIG. 4A shows illustrates an example of hashing and encryption based on the example of arrangement of genomic data for efficient retrieval.

Vault 204 may process contents of applicable format file 212 to generate genomic data hash table 213 and de-identified genomic data 215. In one example, the processing may be performed on the payload data from applicable format file 212. Referring to FIG. 3, the payload data may include, in a tabular format 300, chromosome ID of a strand of chromosome (holding a particular genomic sequence) 301, the position on each strand of chromosome (where the genomic sequence starts) 302, a reference genomic sequence 304, and an alteration from the reference 305. Each reference genomic sequence 304 may include the nucleotide value(s) (A, T, C, or G). Each alteration 205 may include insertions or deletions. The alterations may contain significant differences between subjects. Referring to FIG. 3 and FIG. 4A, chromosome ID 301 and position information 302 may be processed, starting with the prepping steps below to generate the locus information.

In one example 400, all chromosomal position information including the chromosome ID (301) on which a genetic sequence resides and the starting position (302) of the particular genomic sequence on the chromosome (as measured in offset of base pairs) may be padded to fit into a maximum loci space, for example, $2^{33}$, to form data 403. For context, the currently known size of the human genome is approximately 3 billion base pairs and the number of base pairs in a single chromosome is about 249,000,000 base pairs. The space for encoding each chromosome number itself would not exceed $2^5$. The space for encoding each position within a single chromosome would not exceed $2^{28}$. In some implementations, this space of $2^{33}$ encodes all positions of a base pair on each chromosome as well as the chromosomal information of all 23 chromosomes. This space may be padded to $2^{64}$ in order to directly align with modern CPU 64-bit architectures. In these implementations, this encoding space can be further extended to accommodate byte alignment for encryption and hashing operations. A locus may be thus generated in this encoding space as an input object for subsequent encryption and hashing.

Using the locus, both deterministic encryption and probabilistic hashing may be performed. In one instance, deterministic encryption and probabilistic hashing (e.g., locality sensitive hashing) may be performed simultaneously. In one example, an SHA (Secure Hash Algorithm) 256 algorithm may be used for the deterministic encryption. For locality sensitive hashing, MinHash may be used to compute an estimate of the Jaccard similarity coefficient of pairs of input loci. This Jaccard coefficient measures the similarity of input loci as the ratio of the size of their intersection to the size of their union. As discussed herein, the MinHash, as an LSH family for the Jaccard index, projects input loci into sufficiently smaller number of buckets such that highly similar input loci end up in the same bucket. Because of this collision that projects highly similar input loci into the same bucket, the LSH results are not reversible. In some instances, both deterministic encryption and probabilistic hashing functions are used to generate a new in-memory data frame for an input locus.

The processing may then proceed to obfuscate the reference genome 304/404 using, for example, an SHA256 algorithm, an MD5 (Message Digest) algorithm, or other reversible hashing algorithms involving a key. Here, the alteration sequence 305/405 for any non-single-nucleotide-polymorphisms (SNP) may also be encrypted with a SHA256 hash. Using the previously generated set of deterministic hashes, an atomic PUT operation can be performed to enter the set of hashes into a hash table 410, an example of which is shown in FIG. 4B. As illustrated, the key for accessing this hash table 410 is the encrypted genomic data 414. In some cases, encrypted genomic data 414 is a SHA256 hashsum. The value in this hash table 410 is the locus information. Here, an atomic PUT operation means only add the key/value pair to the hash table when the key does not already exist. This hash table 410 may also be referred to as a look-up table. In some cases, in addition to the locus information, de-identified and encrypted patient identifiable information (PII) 412 may also be retrieved from this hash table 410. Additionally, the hash table 410 may contain a token for each patient, which may be retrieved so that the identity of the genetic variant may be recovered, if needed.

Referring again to FIG. 4A, the applicable format file may additionally include header 401, additional meta data created for each sample 402, and metadata for cohort generation and additional analysis. Column level compression may be performed for remaining fields including QUAL, FILTER, and FORMAT (jointly shown as 405 in FIG. 4A) by re-coding to a small integer dictionary (e.g., single byte unsigned integer) to form compressed data 404. Such compression of the de-identified genomic data improving the performance of downstream analysis, reducing both data storage spaces and random access memory sizes necessary to store and process the data, reducing CPU and overall computation time, and reducing the total amount of data transmitted over secured computer networks.

In this illustration, the locality preserving hash may reduce the chromosomal information into smaller dimensions with high collision likelihood and such that hashed values are not reversible. As discussed herein, when the hashed chromosomal information and the encrypted genomic information are unique and sufficient for correlating genetic traits with phenotype traits, including protein expression, propensity to disease, and hereditary traits. Retrieval of identifiable genomic sequence information from the combination of the hashed chromosomal information and the encrypted genomic information, however, is statistically improbable, in the absence of a hash/look-up table. In this manner, all genetic variants can be consistently encoded to create an array of markers that retain information of genetic variation and relative genomic position, without actually containing identifiable sequence data.

This de-identified genomic data 215 may be linked to prescription data 216 from the same patient. In a related note, the prescription data 210 may be processed to de-identify patient identifiable information (214) to provide de-identified data 216. The de-identified genomic data 215 may additionally be linked to other data assets that may be specific to a particular patient and remain in an anonymous manner that is devoid of information capable of identifying the patient.

In this layered diagram, the de-identified genomic data can be compiled and statistically analyzed. Once the analysis results are returned from third party data processing centers, hash table 410 may be looked up by using the set of deterministic hash to retrieve the actual locality information so that the analysis results may be linked to the corresponding actual chromosomal location. The encrypted genomic data may thus be re-mapped to the actual chromosomal location.

Figure 5:
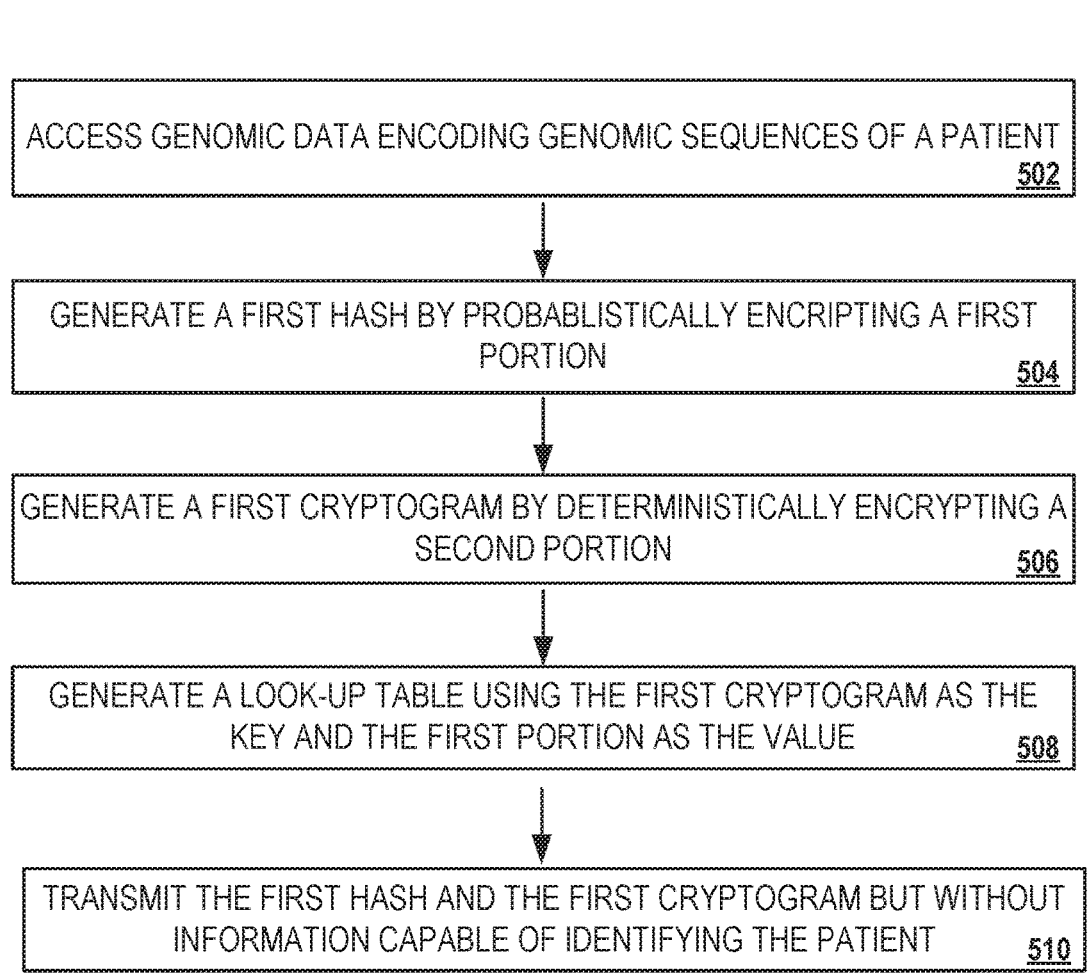
FIG. 5 is a diagram showing an example of a process 500 to preserve patient privacy when analyzing genomic data of a population of patients.

FIG. 5 shows is a diagram showing an example of a process 500 to preserve patient privacy when analyzing genomic data of a population of patients. Briefly, the process 500 includes accessing genomic data that encodes genomic sequences from patients (502); generating a first hash by probabilistically hashing a first portion of the genomic data (504); generating a first cryptogram by deterministically encrypting a second portion of the genomic data (506); generating a look-up table by using the first cryptogram as a key and the first portion of the genomic data as a value (508); and transmitting the first hash and the first cryptogram without information capable of revealing identifiable genomic sequence data (510). As disclosed herein, a cryptogram means the output of an encryption process. In some instances, the encryption process can be a deterministic encryption process. Examples of deterministic encryptions include the use of SHA256 (Secure Hash Algorithm) algorithms, an encryption using symmetric keys, and an encryption based on the PKI (Public Key Infrastructure).

A processor at a data vault 116 (see FIG. 1) may access genomic data that encodes genomic sequences from a population of patients (502). As discussed, the processor at the data vault may convert heterogeneous format of data from participating data partner and medical center (108) into an applicable format file that includes, for each genomic sequence, the ID of the chromosome on which the genomic sequence resides, the starting position of the genomic sequence on the chromosome, the reference genomic sequence, and the alteration/variation from the reference.

The processor may apply a probabilistic hashing to a first portion of the genomic information and generate a first hash (504). The first portion of genomic information may include locus information that encodes, for example, the ID of the chromosome on which the genomic sequence resides, and the starting position of the genomic sequence on the chromosome. The probabilistic hash is a locality-sensitive hash that reduces the input locus information into smaller dimensions such that different loci, depending on similarity measures, may be reduced to the same bucket. Recovery of the first portion of genomic information is statistically improbable outside the processor of the data vault.

The processor may deterministically encrypt a second portion of the genomic information and generate a first cryptogram (506). In one example, this encryption may be based on a symmetric key. In another example, asymmetric encryption involving private/public key pair may be used. In some implementations, hashing algorithms involving the use of a key may be used. Examples of hashing algorithms include various SHA (Secure Hash Algorithm) algorithm and MD (Message Digest) algorithms. The output of the encryption may be known as the cryptogram.

The processor may then construct a look-up table by using the first cryptogram as the key and using the first portion of the genomic information as the value (608). Using this look-up table, the first portion of the genomic information may be retrieved by indexing the look-up table based on the first cryptogram. The look-up table may be exclusive for the data vault.

The processor may then transmit the first cryptogram and the first hash to third-party data processing centers (510). In some cases, the first hash is the locality information of a genomic sequence that is reduced in dimensionality but still retains sufficient distinction. In these cases, the first cryptogram is the encrypted genomic sequence. The combination of the encrypted genomic sequence and the reduced locality index as represented by the first hash enables genomic analysis in a distributed manner.

Like reference symbols in the various drawings indicate like elements.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. In some instances, computers include cloud-based serverless computing in which no individual computer, machine, virtual machine or the like is used to perform a computational task. For example, AWS lambda, and similar stream processing environments use ephemeral containers that spin up, process data, and are spin down. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method, the method comprising:
    accessing, by one or more processors in a data vault, genomic data of patients from a genomic database, the genomic data encoding strings of nucleotide values from genomic sequences of the patients as well as information of respective chromosomes on which corresponding genomic sequences reside;
    generating, by the one or more processors in the data vault, a first hash by probabilistically and irreversibly encrypting a first portion of the genomic data encoding a first genomic sequence of each patient, the first hash projecting the first portion into reduced dimensions such that the first portion of the genomic data encoding the first genomic sequence of each patient becomes statistically improbable to recover outside the one or more processors in the data vault;
    generating, by the one or more processors in the data vault, a first cryptogram by deterministically and reversibly encrypting a second portion of the genomic data encoding the first genomic sequence of each patient;
    generating, by the one or more processors in the data vault, a look-up table by using at least the first cryptogram as a key and the first portion of the genomic data encoding the first genomic sequence of each patient as the value;
    transmitting, by the one or more processors in the data vault, encrypted genomic data that includes the first hash and the first cryptogram to one or more processors outside the data vault without patient identifiable information;
    receiving, from the one or more processors outside the data vault, processed results that include the encrypted genomic data of each patient; and
    decoding, by the one or more processors in the data vault, the encrypted genomic data based on, at least in part, the look-up table to analyze the processed results according to the first portion of the genomic data encoding the first genomic sequence of each patient such that aggregate analysis of the patients are conducted without revealing patient identifiable information of each patient to the one or more processors outside the data vault.

2. The method of claim 1, wherein probabilistically and irreversibly encrypting the first portion comprises probabilistically and irreversibly encrypting locus information that includes an identification (ID) of a particular chromosome on which the first genomic sequence resides as well a starting position of the first genomic sequence on the particular chromosome.

3. The method of claim 2, wherein the information encoding the string of nucleotides values of the particular chromosome includes a reference genome sequence and an alteration sequence.

4. The method of claim 1, wherein deterministically and reversibly encrypting the second portion comprises deterministically and reversibly encrypting strings of nucleotide values from the first genomic sequence.

5. The method of claim 1, further comprising:
    generating, by the one or more processors in the data vault, a second hash by deterministically encrypting the first portion of the genomic data.

6. The method of claim 5, wherein generating the look-up table comprises:
    using the second hash as well as the first cryptogram as a key and the first portion of the genomic data encoding the first genomic sequence as a value such that the first portion of the genomic data encoding the first genomic sequence is retrievable at the one or more processors in the data vault based on the combination of the second hash and the first cryptogram.

7. The method of claim 5, wherein transmitting the information comprises transmitting the information encoding the first hash, the second hash, and the first cryptogram to one or more processors that are different from the one or more processors in the data vault and without patient identifiable information.

8. The method of claim 5, further comprising:
    generating, by the one or more processors in the data vault, a third hash by probabilistically and irreversibly encrypting the first portion of the genomic data encoding a second genomic sequence, the third hash projecting the first portion into reduced dimensions such that the first portion of the genomic data encoding the second genomic sequence becomes statistically improbable to recover outside the one or more processors in the data vault.

9. The method of claim 8, further comprising:
    generating, by the one or more processors in the data vault, a second cryptogram by deterministically and reversibly encrypting a second portion of the genomic data encoding the second genomic sequence.

10. The method of claim 9, further comprising:
    adding, by the one or more processors in the data vault, a new key-value entry to the look-up table using at least the third hash as a key in the new key-value entry and the second cryptogram as a value for the new key-value entry.

11. The method of claim 8, wherein the first hash and the third hash both correspond to chromosomal information from the same patient.

12. The method of claim 8, wherein the first hash and the second hash correspond to chromosomal information from different patients.

13. The method of claim 1, wherein probabilistically and irreversibly encrypting comprises performing a locality-sensitive hashing.

14. The method of claim 1, wherein deterministically and reversibly encrypting the string of nucleotide values comprises using a reversible hash to encrypt the string of nucleotide values.

15. The method of claim 1, wherein deterministically and reversibly encrypting the string of nucleotide values comprises encrypting using a key.

16. A computer system comprising at least one non-transitory storage device and at least one processor coupled thereto, the computer system configured to perform operations of:

accessing, by the at least one processor of the computer system, genomic data of patients from a genomic database, the genomic data encoding strings of nucleotide values from genomic sequences of the patients as well as information of respective chromosomes on which corresponding genomic sequences reside;

generating a first hash by probabilistically and irreversibly encrypting a first portion of the genomic data encoding a first genomic sequence of each patient, the first hash projecting the first portion into reduced dimensions such that the first portion of the genomic data encoding the first genomic sequence of each patient becomes statistically improbable to recover outside the at least one processor of the computer system;

generating a first cryptogram by deterministically and reversibly encrypting a second portion of the genomic data encoding the first genomic sequence of each patient;

generating a look-up table by using at least the first cryptogram as a key and the first portion of the genomic data encoding the first genomic sequence of each patient as the value;

transmitting encrypted genomic data that includes the first hash and the first cryptogram to one or more processors that are different from the at least one processor of the computer system without patient identifiable information;

receiving, from the one or more processors that are different from the computer system, processed results that include the encrypted genomic data of each patient; and decoding the encrypted genomic data based on, at least in part, the look-up table to analyze the processed results according to the first portion of the genomic data encoding the first genomic sequence of each patient such that aggregate analysis of the patients are conducted without revealing patient identifiable information of each patient to the one or more processors that are different from the at least one processor of the computer system.

17. The computer system of claim 16, wherein the operations further comprise:

generating a second hash by deterministically encrypting the first portion of the genomic data.

18. The computer system of claim 17, wherein generating the look-up table comprise:

using the second hash as well as the first cryptogram as a key and the first portion of the genomic data encoding the first genomic sequence as a value such that the first portion of the genomic data encoding the first genomic sequence is retrievable at the computer system based on the combination of the second hash and the first cryptogram.

19. The computer system of claim 17, wherein transmitting the information comprises transmitting the information encoding the first hash, the second hash, and the first cryptogram to one or more processors that are different from the computer system and without patient identifiable information.

20. The computer system of claim 16, wherein the operations further comprise:

generating a third hash by probabilistically and irreversibly encrypting the first portion of a second genomic sequence, the third hash projecting the first portion into reduced dimensions such that the first portion of the genomic data encoding the second genomic sequence becomes statistically improbable to recover outside the at least one processor of the computer system.

21. The computer system of claim 20, wherein the operations further comprise:

generating a second cryptogram by deterministically and reversibly encrypting a second portion of the genomic data encoding the second genomic sequence.

22. The computer system of claim 21, wherein the operations further comprise:

adding, a new key-value entry to the look-up table using at least the third hash as a key in the new key-value entry and the second cryptogram as a value for the new key-value entry.

23. The computer system of claim 16, wherein probabilistically and irreversibly encrypting comprises performing a locality-sensitive hashing.

24. The computer system of claim 16, wherein deterministically and reversibly encrypting the string of nucleotide values comprises using a reversible hash to encrypt the string of nucleotide values.

25. The computer system of claim 16, wherein deterministically and reversibly encrypting the string of nucleotide values comprises encrypting using a key.

26. A non-transitory computer-readable medium comprising software instructions that, when executed by a computer, causes the computer to perform operations of:

accessing, by one or more processors of the computer, genomic data of patients from a genomic database, the genomic data encoding strings of nucleotide values from genomic sequences of the patients as well as information of respective chromosomes on which corresponding genomic sequences reside;

generating a first hash by probabilistically and irreversibly encrypting a first portion of the genomic data encoding a first genomic sequence of each patient, the first hash projecting the first portion into reduced dimensions such that the first portion of the genomic data encoding the first genomic sequence of each patient becomes statistically improbable to recover outside the one or more processors of the computer;

generating a first cryptogram by deterministically and reversibly encrypting a second portion of the genomic data encoding the first genomic sequence of each patient;

generating a look-up table by using at least the first cryptogram as a key and the first portion of the genomic data encoding the first genomic sequence of each patient as the value;

transmitting encrypted genomic data that includes the first hash and the first cryptogram to one or more processors that are different from the one of more processors of the computer without patient identifiable information;

receiving, from the one or more processors that are different from the one or more processors of the computer, processed results that include the encrypted genomic data of each patient; and decoding the encrypted genomic data based on, at least in part, the look-up table to analyze the processed results according to the first portion of the genomic data encoding the first genomic sequence of each patient such that aggregate analysis of the patients are conducted without revealing patient identifiable information of each patient to the one or more processors that are different from the one or more processors of the computer.

* * * * *